(12) United States Patent
Tang et al.

(10) Patent No.: US 10,640,492 B2
(45) Date of Patent: May 5, 2020

(54) TUBULIN INHIBITOR

(71) Applicant: SHENZHEN NEPTUNUS PHARMACEUTICAL RESEARCH INSTITUTE CO., LTD., Shenzhen, Guangdong (CN)

(72) Inventors: Tian Tang, Guangdong (CN); Yanqing Wang, Guangdong (CN); Xiaorou Liu, Guangdong (CN); Jin Wang, Guangdong (CN); Ruyi Jin, Guangdong (CN); Hanlin Feng, Guangdong (CN)

(73) Assignee: SHENZHEN NEPTUNUS PHARMACEUTICAL RESEARCH INSTITUTE CO., LTD., Shenzhen, Guangdong (CN)

( * ) Notice: Subject to any disclaimer, the term of this patent is extended or adjusted under 35 U.S.C. 154(b) by 0 days.

(21) Appl. No.: 16/340,666

(22) PCT Filed: Sep. 29, 2017

(86) PCT No.: PCT/CN2017/104316
§ 371 (c)(1),
(2) Date: Apr. 9, 2019

(87) PCT Pub. No.: WO2018/068666
PCT Pub. Date: Apr. 19, 2018

(65) Prior Publication Data
US 2019/0225595 A1  Jul. 25, 2019

(30) Foreign Application Priority Data
Oct. 11, 2016  (CN) .......................... 2016 1 0890235

(51) Int. Cl.
*A61K 31/497* (2006.01)
*C07D 403/06* (2006.01)
*A61P 35/00* (2006.01)
*A61K 31/496* (2006.01)
*A61K 31/337* (2006.01)

(52) U.S. Cl.
CPC .......... *C07D 403/06* (2013.01); *A61K 31/337* (2013.01); *A61K 31/496* (2013.01); *A61P 35/00* (2018.01)

(58) Field of Classification Search
CPC ........................... A61K 31/497; C07D 403/06
USPC ...................................... 514/255.05; 544/405
See application file for complete search history.

(56) References Cited

FOREIGN PATENT DOCUMENTS

| CN | 1684955 A | 10/2005 |
|---|---|---|
| WO | WO2007035841 A1 | 3/2007 |
| WO | 106565686 A | 4/2017 |

*Primary Examiner* — Jeffrey H Murray
(74) *Attorney, Agent, or Firm* — Greer, Burns & Crain Ltd.

(57) ABSTRACT

Provided are a new tubulin inhibitor and applications thereof, the tubulin inhibitor being a series of compounds based on substituted heterocyclic skeletons, targeting the colchicine binding sites of tubulin. The structure is: Formula (I), wherein: formula (A), n independently expresses an integer between 0 and 5, the condition being that n≤5, A represents mono- or poly-substituted groups, the groups being selected from the group consisting of H, C1-C20 amide group, C1-C20 acyloxy group, C1-C20 alkanoyl group, C1-C20 alkoxycarbonyl group, C1-C20 alkoxy group, C1-C20 alkylamino group, C1-C20 alkylcarboxyamino group, aroyl group, aralkanoyl group, carboxyl group, cyano group, halogen group, hydroxyl group, nitro group and methylthienyl group.

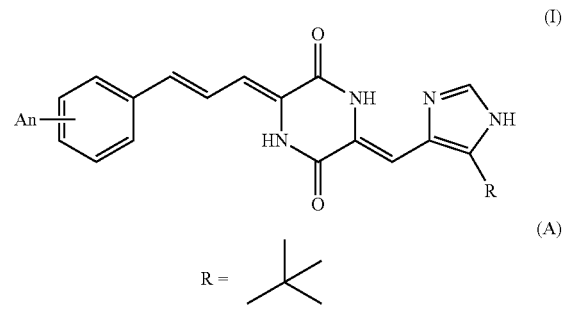

7 Claims, 3 Drawing Sheets

TUBULIN INHIBITOR

BACKGROUND

The present invention relates to the field of medicine, and in particular to a novel series of compounds as tubulin inhibitors and uses thereof.

The invention further relates to a pharmaceutical composition comprising the compounds.

As the main means of cancer treatment, anti-tumor drugs have made considerable contributions to prolonging the survival time of patients and improving their quality of life. Among them, the drugs acting on microtubules (microtubule inhibitors) have a very important status in oncology drugs. However, the current clinical drugs are accompanied with the following unfavorable problems: poor water solubility, inconvenient drug administration, easy to cause allergic reactions, reduced efficacy caused by serious toxic side effects and acquired resistance, and low production due to the difficulty in synthesis of the complicated chemical structures, which all limit their further use. Therefore, there is an urgent need to find novel tubulin inhibitors, especially small molecule inhibitors with simple structures.

Microtubules are important component of eukaryotic cells and important target for antitumor drugs. Microtubules are a major component in the cytoskeleton and made up of α-tubulin and β-tubulin heterodimers, having the hollow tubular structure characteristics. In addition, there is a γ tubulin, which is not a component of microtubules but participates in the assembly of microtubules.

Microtubules have the dynamic properties of polymerization and depolymerization, and play an important role in cell morphology, cell division, signal transduction and material transport. The microtubules polymerize into a spindle in the early stage of cell division, which in the mitosis pulls the chromosome towards two poles and moves into two daughter cells to complete the cell proliferation. Since microtubules play an extremely important role in cell division, now they have become one of the important targets for antitumor drug research. Tubulin inhibitors acting on microtubule systems have also become a class of effective antitumor drugs.

There are two classification methods for tubulin inhibitors. One is to divide them into two categories based on different functional mechanisms: ① tubulin depolymerization agent that inhibits the tubulin polymerization; ② tubulin polymerization agent that promotes the tubulin polymerization. Another classification method is to divide them into three categories based on different action sites of tubulin inhibitor on tubulin: ① tubulin inhibitors acting on the colchicine site; ② tubulin inhibitors acting on the vinblastine site; ③ tubulin inhibitors acting on the paclitaxel site.

Existing studies have shown that there are three major drug binding sites in tubulins: the taxol-binding site (Taxol site), the vinblastine-binding site (Vinblastine site), and the colchieine-binding site (Colchieine site). Among the three sites, the Colchicine site is valuable for the study of small molecule anti-tumor inhibitors due to the small volume of its binding cavity.

Chinese patent application CN1684955 relates to a compound for the treatment of cancers and fungal infections, dehydrophenylahistins (pinabulin) (Formula II), which can be used as a cell cycle inhibitor, tumor-growth inhibitor or fungal inhibitor.

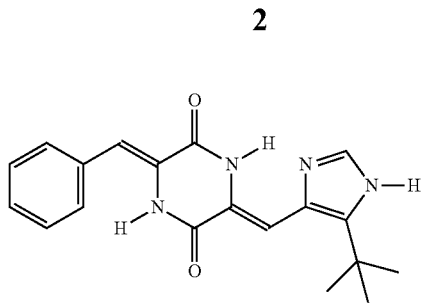

Formula (II)

Chinese patent application CN1934101A relates to the use of the above compound for reducing vascular proliferation and vascular density, acting on tumor blood vessels. But plinabulin, when used alone, has a minor inhibitory effect on tumors and causes a lot of disturbance to the immune system function.

SUMMARY

It is an object of the present invention to provide a novel tubulin inhibitor targeting the colchicines-binding site, which is a series of compounds based on a substituted heterocyclic backbone.

By analyzing the structural properties of the binding sites and the binding modes of inhibitors, the properties of the sub-pockets and their key functional residues and potential binding sites are identified. Starting from the prevalent groups in the inhibitor structures, a structural template for the inhibitor is presented by optimizing the prevalent structure iteratively. Then, starting from the active conformations combined with the existing structure-activity relationship studies, the three-dimensional pharmacophore model of the inhibitor and some structural factors affecting the activity are proposed. Accordingly, the studies on design, synthesis, structural modification and in vitro activity of novel microtubule inhibitors are developed.

The present invention also provides a pharmaceutical composition comprising above tubulin inhibitors.

According to above mentioned object of the present invention, it is a tubulin inhibitor having the structure of Formula (I):

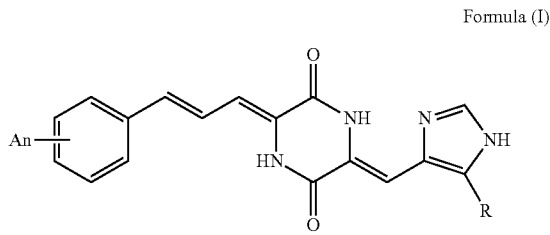

Formula (I)

wherein:

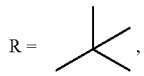

$R = $ n independently represents an integer of 0 to 5, with the proviso that n≤5, A represents a mono- or poly-substituted group selected from the group consisting of H, $C_1$-$C_{20}$ alkyl, $C_1$-$C_{20}$ hydrocarbyl, $C_1$-$C_{20}$ acylamino, $C_1$-$C_{20}$ acyloxy, $C_1$-$C_{20}$ alkanoyl, $C_1$-$C_{20}$ alkoxycarbonyl, $C_1$-$C_{20}$ alkoxy, $C_1$-$C_{20}$ alkylamino, $C_1$-$C_{20}$ alkylcarboxyamino, aroyl, aralkanoyl, carboxyl, cyano, halogen, hydroxy, nitro and methylthienyl.

More preferably, in the above Formula (I), n independently represents an integer of 0 to 2, with the proviso that n≤2, A represents a mono- or poly-substituted group selected from the group consisting of H, vinyl, methyl, trifluoromethoxy, methoxy, cyano, halogen and benzoyl.

Representative compounds of the invention include:
(3Z,6Z)-3-((E)-3-(5-tert-butyl)-1H-imidazolyl-4-yl)methylene)-6-((E)-3-(3-ethylenephenyl)-2-propenylene)piperazine-2,5-dione (6);
(3Z,6Z)-3-((E)-3-(5-tert-butyl)-1H-imidazolyl-4-yl)methylene)-6-((E)-3-(3-fluorophenyl)-2-propenylene)piperazine-2,5-dione (7);
(3Z,6Z)-3-((E)-3-(5-tert-butyl)-1H-imidazolyl-4-yl)methylene)-6-((E)-3-phenylpropenylene)piperazine-2,5-dione (8);
(3Z,6Z)-3-((E)-3-(5-tert-butyl)-1H-imidazolyl-4-yl)methylene)-6-((E)-3-(2,3-dimethylphenyl)-2-propenylene)piperazine-2,5-dione (9);
(3Z,6Z)-3-((E)-3-(5-tert-butyl)-1H-imidazolyl-4-yl)methylene)-6-((E)-3-(4-trifluoromethoxyphenyl)-2-propenylene)piperazine-2,5-dione (10);
(3Z,6Z)-3-((E)-3-(5-tert-butyl)-1H-imidazolyl-4-yl)methylene)-6-((E)-3-(2,5-difluorophenyl)-2-propenylene)piperazine-2,5-dione (11);
(3Z,6Z)-3-((E)-3-(5-tert-butyl)-1H-imidazolyl-4-yl)methylene)-6-((E)-3-(4-methoxyphenyl)-2-propenylene)piperazine-2,5-dione (12);
(3Z,6Z)-3-((E)-3-(5-tert-butyl)-1H-imidazolyl-4-yl)methylene)-6-((E)-3-(3,5-dimethoxyphenyl)-2-propenylene)piperazine-2,5-dione (13);
(3Z,6Z)-3-((E)-3-(5-tert-butyl)-1H-imidazolyl-4-yl)methylene)-6-((E)-3-(3-chlorophenyl)-2-propenylene)piperazine-2,5-dione (14);
(3Z,6Z)-3-((E)-3-(5-tert-butyl)-1H-imidazolyl-4-yl)methylene)-6-((E)-3-(3-cyanophenyl)-2-propenylene)piperazine-2,5-dione (15);
(3Z,6Z)-3-((E)-3-(5-tert-butyl)-1H-imidazolyl-4-yl)methylene)-6-((E)-3-(3-benzoylphenyl)-2-propenylene)piperazine-2,5-dione (16);
(3Z,6Z)-3-((E)-3-(5-tert-butyl)-1H-imidazolyl-4-yl)methylene)-6-((E)-3-(2-chloro-5-fluorophenyl)-2-propenylene)piperazine-2,5-dione (17);
(3Z,6Z)-3-((E)-3-(5-tert-butyl)-1H-imidazolyl-4-yl)methylene)-6-((E)-3-(3-methoxy-4-acetoxy)-2-propenylene)piperazine-2,5-dione (18);

The preparation method of the compounds of the present invention is exemplified below by taking the representative compound 10 of the present invention as an example. The synthetic route 1 of the present invention is as follows:

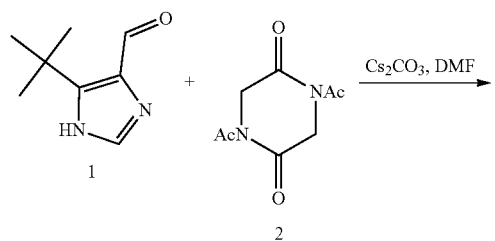

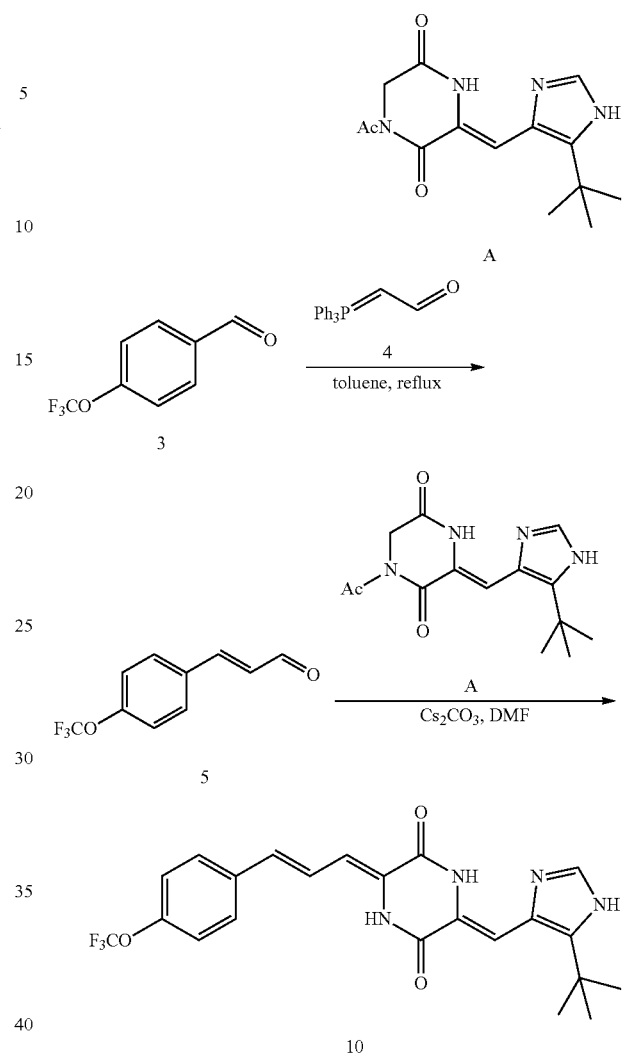

According to the method of Route 1, the following representative compounds of the present invention are synthesized:

TABLE 1

| Compound No. | Compound structure Structure |
|---|---|
| 6 | |

TABLE 1-continued

Compound structure

| Compound No. | Structure |
|---|---|
| 7 | (3-fluorophenyl)-vinyl-piperazine-2,5-dione with (5-tert-butyl-1H-imidazol-4-yl)methylene |
| 8 | phenyl-vinyl-piperazine-2,5-dione with (5-tert-butyl-1H-imidazol-4-yl)methylene |
| 9 | (2,3-dimethylphenyl)-vinyl-piperazine-2,5-dione with (5-tert-butyl-1H-imidazol-4-yl)methylene |
| 10 | (4-trifluoromethoxyphenyl)-vinyl-piperazine-2,5-dione with (5-tert-butyl-1H-imidazol-4-yl)methylene |
| 11 | (2,5-difluorophenyl)-vinyl-piperazine-2,5-dione with (5-tert-butyl-1H-imidazol-4-yl)methylene |
| 12 | (4-methoxyphenyl)-vinyl-piperazine-2,5-dione with (5-tert-butyl-1H-imidazol-4-yl)methylene |
| 13 | (3,5-dimethoxyphenyl)-vinyl-piperazine-2,5-dione with (5-tert-butyl-1H-imidazol-4-yl)methylene |
| 14 | (3-chlorophenyl)-vinyl-piperazine-2,5-dione with (5-tert-butyl-1H-imidazol-4-yl)methylene |
| 15 | (3-cyanophenyl)-vinyl-piperazine-2,5-dione with (5-tert-butyl-1H-imidazol-4-yl)methylene |
| 16 | (3-benzoylphenyl)-vinyl-piperazine-2,5-dione with (5-tert-butyl-1H-imidazol-4-yl)methylene |
| 17 | (2-chloro-5-fluorophenyl)-vinyl-piperazine-2,5-dione with (5-tert-butyl-1H-imidazol-4-yl)methylene |
| 18 | (3-methoxy-4-acetoxyphenyl)-vinyl-piperazine-2,5-dione with (5-tert-butyl-1H-imidazol-4-yl)methylene |

Another object of the present invention is to provide a pharmaceutical composition comprising the therapeutically effective amount of the compound of Formula (I) and pharmaceutically acceptable carrier and/or excipients, for the treatment of various cancers, infections, inflammations and conventional proliferative diseases, or the treatment of other diseases characterized by the appearance of rapidly proliferating cells such as psoriasis and other skin diseases. The mentioned therapeutically effective amount means that the amount of the compound of Formula (I) in the pharmaceutical composition is sufficient to produce a clinically desired therapeutic effect, for example, the tumor size of the patient is reduced to a clinically acceptable range, or the treatment of other diseases is clinically recognized as effective.

In a specific embodiment, the compounds or pharmaceutical compositions of the invention are used to treat sarcomas, carcinomas and/or leukemias. Exemplary conditions in which the compound or composition can be used alone or as part of a therapeutic regimen include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatocellular carcinoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma.

In some specific embodiments, the compounds or compositions of the present invention are used to treat conditions such as cancers formed in breast, prostate, kidney, bladder, or colon tissue.

In other specific embodiments, the compounds or pharmaceutical compositions of the present invention are used to treat proliferative or neoplastic diseases occurring in adipose tissue, such as adipocyte tumors (lipomas), fibroids, lipoblastoma, hyperlipidemia, brown lipoma (hibemomas), hemangiomas and/or liposarcoma.

In some embodiments, the compositions and compounds can also be used to control infectious agents and parasites (e.g., bacteria, trypanosomes, fungi, etc.).

The pharmaceutical composition of the present invention can be administered for example, by intravenous, intradermal, intramuscular, subcutaneous, oral or inhalation route. The dosage form of the pharmaceutical composition could be a gastrointestinal preparation such as tablet, capsule or pill. Alternatively, it could be a parenteral preparation such as an injection or an external preparation.

Furthermore, the present invention provides a method of treating tumors and related diseases. The method consists administering the therapeutically effective amount of the compound of Formula (I) to a patient with cancer or related conditions.

The present invention also provides a method of modulating microtubule polymerization in patients. The method involves administering a therapeutically effective amount of at least one compound of the present invention or the pharmaceutically acceptable prodrug, salt, hydrate, solvate, crystalline form or diastereomer of the compounds.

The compounds of the present invention can be used in combination with chemotherapeutic agents for the treatment of tumors. Experiments have demonstrated that the compounds of the present invention can enhance the tumor suppressing effect when used in combination with a chemotherapeutic agent, and reduce the toxicity of the chemotherapeutic agent at the same time. The most preferred compound is compound (17), and the chemotherapeutic agent can be a conventional chemotherapeutic agent commonly used for treating tumors. In a preferred embodiment, compound (17) is used in combination with docetaxel to produce a very good therapeutic effect.

The compounds of the invention can bind to tubulin, inhibit the growth and proliferation of the cancer cells, while having almost no influence on the corresponding leukocytes and granulocytes. The compounds have less disturbance to immune system functions when fighting against tumor proliferation, and successfully overcome the deficiencies of the anti-tumor drugs in clinical use. Such compounds are also useful in the treatment of other conditions associated with hyperproliferation.

A: Inhibitory effect of the compound on tumor proliferation in nude mice; B: Effect of the compound on tumor weight in nude mice while inhibiting the tumor proliferation; C: Effect on the neutrophil count in SD rats after continuous administration of compound (17) in combination with docetaxel.

Figure 3:
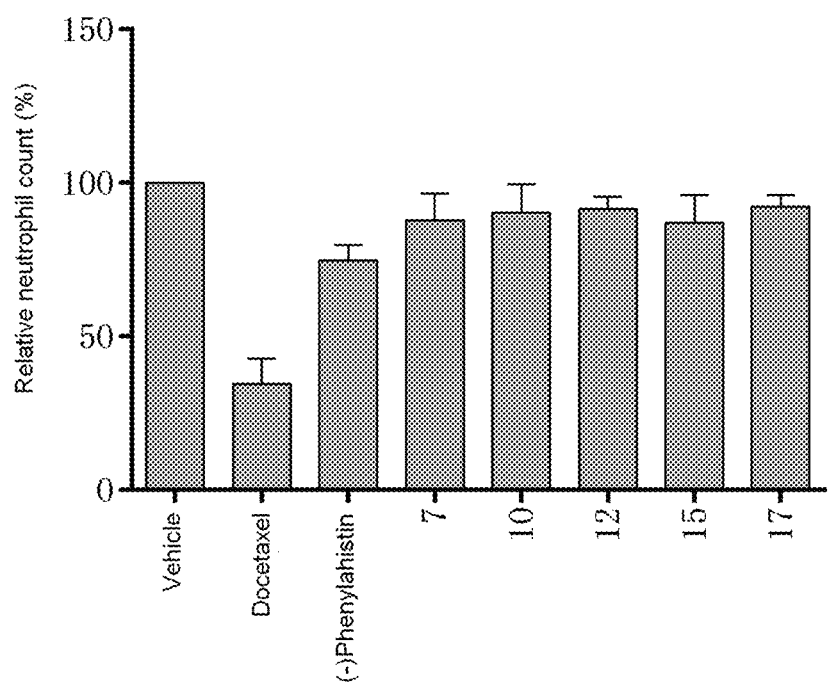

FIG. 3 shows the effect of each compound on the relative neutrophil count in rats using an equivalent tumor inhibition dose.

DETAILED DESCRIPTION

The structural modification of the compounds of the present invention is based on the structure of the above compound of Formula (II). And the key point of the modification is that one side chain of the piperazine ring was extended by introducing a double bond to form a new carbon chain with two double bonds and two single bonds. The experimental results show that this modification enhances the inhibitory ability of the new compounds on tumor cells, while has no influence on the functions of leukocytes and granulocytes, which leads to a better anti-tumor effect. Comparing the test results of the modified compounds to the original compounds having a single and a double bond on the side chain to be modified, it is shown that the latter compounds are unstable and degrade easily at normal temperature, thus the compounds of the present invention have better stability.

The present invention is further illustrated by the following examples, but these examples are not forming any limitation towards the scope of the invention.

General methods: The melting point was measured on an RT-1 melting point apparatus (Tianjin Analytical Instrument Factory) with the temperature had been corrected. 1H NMR spectra were recorded on a Bruker AV400 (400 MHz) spectrometer and described as a low magnetic field in parts per million (ppm) of TMS. Infrared spectra were recorded on a Nicolet Magna 550FT-IR Fourier spectrophotometer. Mass spectra were recorded on a HP1100 Esquire 2000 liquid chromatography/mass spectrometer. UV spectra were recorded on a Shimadzu UV2410 spectrophotometer. TLC was performed on silica gel GF254 high efficiency plates (Yantai Zhifu Silica Gel Development Test Plant). The optical rotation measurement was performed on a WZZ-1S optical rotation measuring instrument (Shanghai Precision Scientific Instrument Co., Ltd.).

In the examples, the compounds of Formula (I) were synthesized according to Route 1.

Example 1

Step 1:

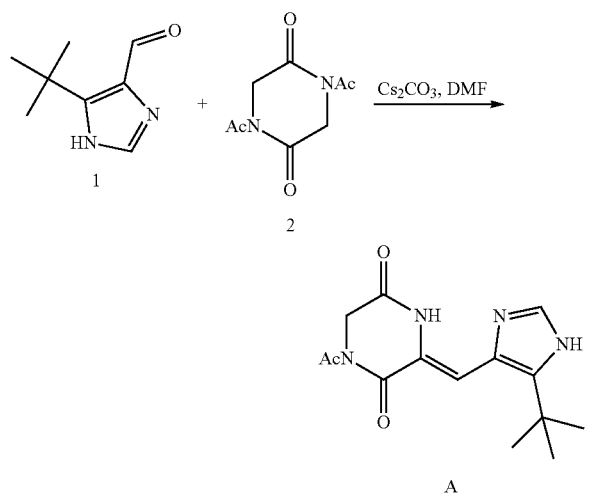

Preparation of Compound A was referred to the synthetic Route A of the Example 2 described in Chinese Patent No. CN1684955.

Step 2:

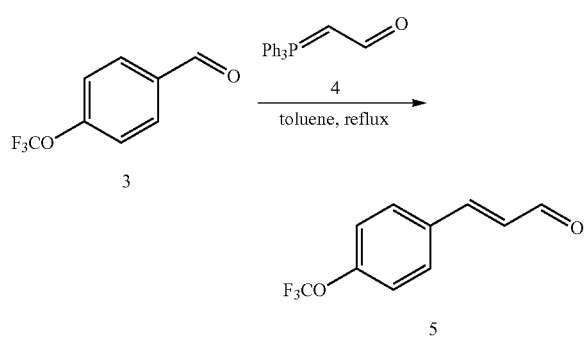

4-trifluoromethoxybenzaldehyde 3 (19.0 g, 0.10 mol), formyl methylenetriphenylphosphane 4 (33.5 g, 0.11 mmol) and toluene (200 ml) were added to a 1 L dry single-necked flask. The reaction system was refluxed for 17 hours and then concentrated to obtain crude product which was purified by column chromatography (eluent: petroleum ether/ethyl acetate: 100/1 to 80/20) to obtain yellow oil 5 (14.9 g, yield: 69%). ESI-MS: m/z=217.1 (M+H)+.

Step 3:

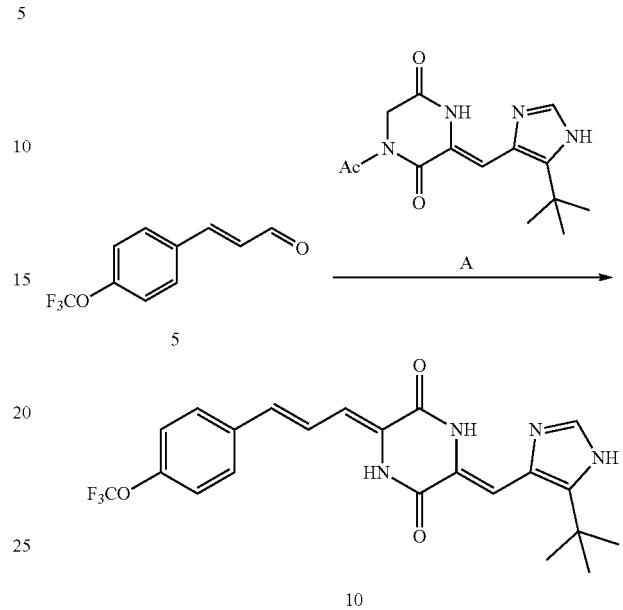

DMF (100 ml), intermediate A (1.38 g, 5 mmol), 3-(4-trifluoromethoxyphenyl)propenal 5 (2.16 g, 10 mmol) and carbonic acid (3.26 g, 10 mmol) were added to a 250 ml dry single-necked flask. The reaction system was stirred at 25° C. for 12 hours. The mixture was cooled to room temperature, poured into ice water, and then extracted with ethyl acetate. The organic layer was washed three times with brine, dried with anhydrous sodium sulfate, filtered and concentrated to obtain crude product. The crude product was washed with petroleum ether/ethyl acetate (5/1) to obtain bright yellow solid 10 (1.69 mg, yield: 38%). ESI-MS: m/z=447.2 (M+H)+; $^1$H-NMR: (500 MHz, DMSO-$d_6$) δ7.84-7.78 (m, 2H), 7.70-7.68 (d, J=8.4 Hz, 2H), 7.38-7.36 (d, J=8.4 Hz, 2H), 6.93-6.89 (d, J=15.6 Hz, 1H), 6.88-6.85 (m, 1H), 6.53-6.50 (d, J=12 Hz, 1H), 1.38 (s, 9H).

Examples 2~11

The intermediate A was prepared in Steps 1~2, which is identical to the Steps 1~2 of Example 1. The preparation methods of other intermediates and final products are listed in the following table:

TABLE 2

Preparation methods of other compounds

| No. | Amount of reactant 1 | Amount of reactant 2 or 3 | Solvent volume | Reaction condition | Post-treatment | Yield | Intermediate of final product structure |
|---|---|---|---|---|---|---|---|
| Example 2 Step 2 | 3-vinylbenzaldehyde 0.10 mol | Ph₃P=CHCHO 0.11 mol | Toluene 200 ml | Heated to reflux for 17 h | Spin-drying, then column chromatography (eluent: volume ratio of petroleum ether/ethyl acetate: 100/1 to 80/20) | 60% | (3-vinylcinnamaldehyde) |
| Example 2 Step 3 | A 5 mmol | 1) 3-vinylcinnamaldehyde 10 mmol; 2) Cs₂CO₃ 10 mmol | DMF 100 ml | Stirred for 2 h at 25~30° C. | Cooled to room temperature, poured into ice water. Extracted with ethyl acetate, the organic phase washed with brine, dried, filtered, and concentrated. Crude product was washed with dichloromethane/methanol (10/1) | 40% | Compound 6 |
| Example 3 Step 2 | 3-fluorobenzaldehyde 0.10 mol | Ph₃P=CHCHO 0.11 mol | Toluene 200 ml | Heated to reflux for 16 h | Spin-drying, then column chromatography (eluent: volume ratio of petroleum ether/ethyl acetate: 100/1 to 80/20) | 62% | (3-fluorocinnamaldehyde) |
| Example 3 Step 3 | A 5 mmol | 1) 3-fluorocinnamaldehyde 10 mmol; 2) Cs₂CO₃ 10 mmol | DMF 100 ml | Stirred for 2 h at 25~30° C. | Cooled to room temperature, poured into ice water. Extracted with ethyl acetate, the organic phase washed with brine, dried, filtered, and concentrated. Crude product was washed with dichloromethane/methanol (10/1) | 38% | Compound 7 |
| Example 4 Step 2 | benzaldehyde 0.10 mol | Ph₃P=CHCHO 0.11 mol | Toluene 200 ml | Heated to reflux for 15 h | Spin-drying, then column chromatography (eluent: volume ratio of petroleum ether/ethyl acetate: 100/1 to 80/20) | 58% | cinnamaldehyde |

TABLE 2-continued

Preparation methods of other compounds

| No. | Amount of reactant 1 | Amount of reactant 2 or 3 | Solvent volume | Reaction condition | Post-treatment | Yield | Intermediate of final product structure |
|---|---|---|---|---|---|---|---|
| Example 4 Step 3 | A 5 mmol | 1) [cinnamaldehyde] 10 mmol 2) Cs₂CO₃ 10 mmol | DMF 100 ml | Stirred for 2 h at 25~30° C. | Cooled to room temperature, poured into ice water. Extracted with ethyl acetate, the organic phase washed with brine, dried, filtered, and concentrated. Crude product was washed with dichloromethane/methanol (10/1) | 36% | 8 |
| Example 5 Step 2 | [2,3-dimethylbenzaldehyde] 0.10 mol | Ph₃P=CHCHO 0.11 mol | Toluene 200 ml | Heated to reflux for 17 h | Spin-drying, then column chromatography (eluent: volume ratio of petroleum ether/ethyl acetate: 100/1 to 80/20) | 60% | |
| Example 5 Step 3 | A 5 mmol | 1) [2,3-dimethylcinnamaldehyde] 10 mmol 2) Cs₂CO₃ 10 mmol | DMF 100 ml | Stirred for 2 h at 25~30° C. | Cooled to room temperature, poured into ice water. Extracted with ethyl acetate, the organic phase washed with brine, dried, filtered, and concentrated. Crude product was washed with dichloromethane/methanol (10/1) | 43% | 9 |
| Example 6 Step 2 | [2,5-difluorobenzaldehyde] 0.10 mol | Ph₃P=CHCHO 0.11 mol | Toluene 200 ml | Heated to reflux for 17 h | Spin-drying, then column chromatography (eluent: volume ratio of petroleum ether/ethyl acetate: 100/1 to 80/20) | 62% | |

TABLE 2-continued

Preparation methods of other compounds

| No. | Amount of reactant 1 | Amount of reactant 2 or 3 | Solvent volume | Reaction condition | Post-treatment | Yield | Intermediate of final product structure |
|---|---|---|---|---|---|---|---|
| Example 6 Step 3 | 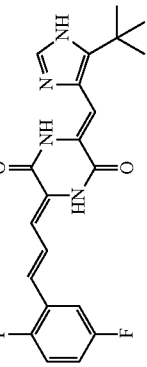 A 5 mmol | 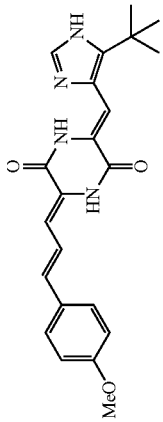 10 mmol 2) Cs₂CO₃ 10 mmol | DMF 100 ml | Stirred for 2 h at 25~30° C. | Cooled to room temperature, poured into ice water. Extracted with ethyl acetate, the organic phase washed with brine, dried, filtered, and concentrated. Crude product was washed with dichloromethane/ methanol (10/1) | 40% | 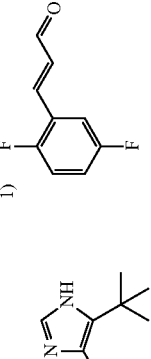 11 |
| Example 7 Step 2 | 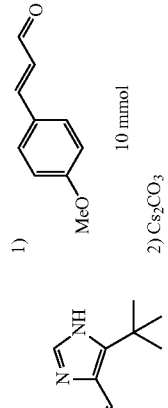 0.10 mol | Ph₃P 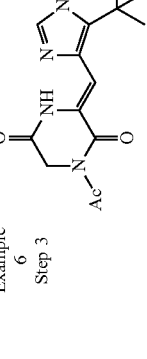 0.11 mol | Toluene 200 ml | Heated to reflux for 17 h | Spin-drying, then column chromatography (eluent: volume ratio of petroleum ether/ethyl acetate: 100/1 to 80/20) | 67% | 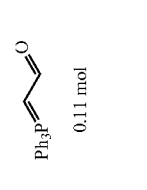 |
| Example 7 Step 3 | 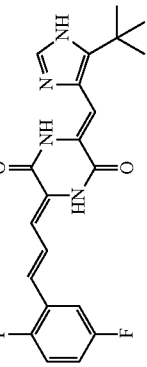 A 5 mmol | 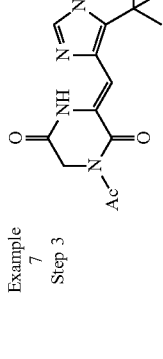 10 mmol 2) Cs₂CO₃ 10 mmol | DMF 100 ml | Stirred for 2 h at 25~30° C. | Cooled to room temperature, poured into ice water. Extracted with ethyl acetate, the organic phase washed with brine, dried, filtered, and concentrated. Crude product was washed with dichloromethane/ methanol (10/1) | 32% | 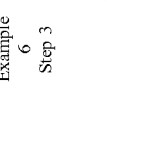 12 |
| Example 8 Step 2 | 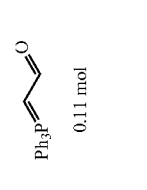 0.10 mol | Ph₃P 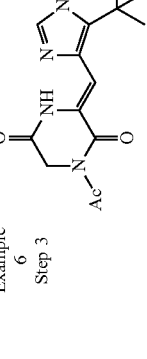 0.11 mol | Toluene 200 ml | Heated to reflux for 17 h | Spin-drying, then column chromatography (eluent: volume ratio of petroleum ether/ethyl acetate: 100/1 to 80/20) | 66% | |

TABLE 2-continued

Preparation methods of other compounds

| No. | Amount of reactant 1 | Amount of reactant 2 or 3 | Solvent volume | Reaction condition | Post-treatment | Yield | Intermediate of final product structure |
|---|---|---|---|---|---|---|---|
| Example 8 Step 3 | A 5 mmol | 1) MeO-C6H3(OMe)-CH=CH-CHO 10 mmol; 2) Cs2CO3 10 mmol | DMF 100 ml | Stirred for 2 h at 25–30° C. | Cooled to room temperature, poured into ice water. Extracted with ethyl acetate, the organic phase washed with brine, dried, filtered, and concentrated. The crude product was washed with dichloromethane/methanol (10/1) | 30% | 13 |
| Example 9 Step 2 | 3-Cl-C6H4-CHO 0.10 mol | Ph3P=CH-CHO 0.11 mol | Toluene 200 ml | Heated to reflux for 17 h | Spin-drying, then column chromatography (eluent: volume ratio of petroleum ether/ethyl acetate: 100/1 to 80/20) | 58% | |
| Example 9 Step 3 | A 5 mmol | 1) Cl-C6H4-CH=CH-CHO 10 mmol; 2) Cs2CO3 10 mmol | DMF 100 ml | Stirred for 16 h at room temperature | Extracted with ethyl acetate, the organic phase washed with brine, dried, filtered, and concentrated. Crude product was washed with dichloromethane/methanol (10/1) | 39% | 14 |
| Example 10 Step 2 | 3-NC-C6H4-CHO 0.10 mol | Ph3P=CH-CHO 0.11 mol | Toluene 200 ml | Heated to reflux for 17 h | Spin-drying, then column chromatography (eluent: volume ratio of petroleum ether/ethyl acetate: 100/1 to 80/20) | 65% | |
| Example 10 Step 3 | A 5 mmol | 1) NC-C6H4-CH=CH-CHO 10 mmol; 2) Cs2CO3 10 mmol | DMF 100 ml | Stirred for 12 h at 25–30° C. | Cooled to room temperature, poured into ice water. Extracted with ethyl acetate, the organic phase washed with brine, dried, filtered, and concentrated. Crude product was washed with dichloromethane/methanol (10/1) | 36% | 15 |

TABLE 2-continued

| No. | Amount of reactant 1 | Amount of reactant 2 or 3 | Solvent volume | Reaction condition | Post-treatment | Yield | Intermediate of final product structure |
|---|---|---|---|---|---|---|---|
| Example 11 Step 2 | 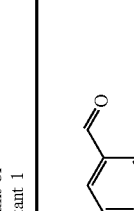 0.10 mol |  0.11 mol | Toluene 200 ml | Heated to reflux for 17 h | Spin-drying, then column chromatography (eluent: volume ratio of petroleum ether/ethyl acetate: 100/1 to 80/20) | 57% | 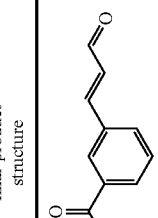 |
| Example 11 Step 3 | 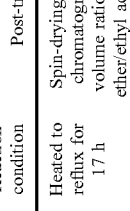 A 5 mmol | 1) 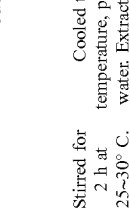 10 mmol 2) Cs₂CO₃ 10 mmol | DMF 100 ml | Stirred for 2 h at 25~30° C. | Cooled to room temperature, poured into ice water. Extracted with ethyl acetate, the organic phase washed with brine, dried, filtered, and concentrated. Crude product was washed with dichloromethane/methanol (10/1) | 41% | 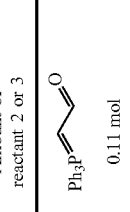 16 |
| Example 12 Step 2 | 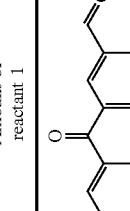 0.10 mol | 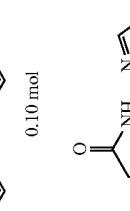 0.11 mol | Toluene 200 ml | Heated to reflux for 17 h | Spin-drying, then column chromatography (eluent: volume ratio of petroleum ether/ethyl acetate: 100/1 to 80/20) | 70% | 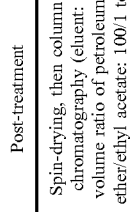 |
| Example 12 Step 3 | 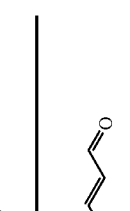 A 5 mmol | 1)  10 mmol 2) Cs₂CO₃ 10 mmol | DMF 100 ml | Stirred for 2 h at 0~5° C. | Extracted with ethyl acetate, the organic phase washed with brine, dried, filtered, and concentrated. Crude product was washed with dichloromethane/methanol (20/1) | 32% | 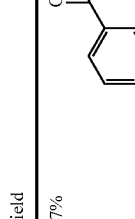 17 |

TABLE 2-continued
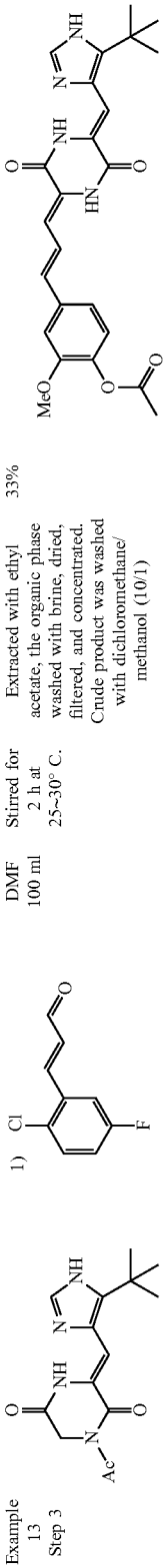

Example 14: Cell Level Inhibition Experiment

Objective:

To test the cytotoxic IC50 values of 14 candidate compounds against 5 cell strains (MDA-MB-231, HT-1080, AGS, A-673 & HUVEC) using a CCK-8 test kit.

Materials and Methods:

Cell Lines:

MDA-MB-231 human breast cancer cell strain (purchased from Shanghai Cell Resource Center, Chinese Academy of Sciences)

T-1080 human fibrosarcoma cell strain (purchased from Shanghai Cell Resource Center, Chinese Academy of Sciences)

AGS human gastric adenocarcinoma cell strain (purchased from Shanghai Cell Resource Center, Chinese Academy of Sciences)

A-673 human rhabdomyosarcoma cell strain (purchased from Shanghai Cell Resource Center, Chinese Academy of Sciences)

HUVEC human umbilical vein endothelial cell strain (purchased from ScienCell Research Laboratories, Cat #8000, Lot #11233)

Reagents and Materials:

Cell Counting Kit-8 (Cat # CK04-13, Dojindo)

96-well culture plate (Cat #3599, Corning Costar)

Medium and fetal bovine serum (GIBCO)

Medium: ECM Endothelial cell medium (Cat #1001, ScienCell Research Laboratories)

Benchtop Microplate Reader: SpectraMax M5 Microplate Reader (Molecular Devices)

EXPERIMENTAL PROCEDURE

Reagent Preparation
Preparation of Medium

| Cell line | Medium |
|---|---|
| MDA-MB-231 | DMEM + 10% FBS |
| HT-1080 | MEM + 10% FBS |
| AGS | F12K + 10% FBS |
| A-673 | DMEM + 10% FBS |
| HUVEC | ECM containing 5% Fetal Bovine Serum (500 ml basal medium + 25 ml FBS + 5 ml ECGS + 5 ml Penicillin/Streptomycin) |

Preparation of the Compound:

a) The compound was serially diluted with DMSO starting from 0.5 μM, using twice echelon dilution.

IC50 Experiment (CCK-8 Detection)

The logarithmic growth phase cells were collected and counted. The cells were re-suspended in complete medium, whose concentration was adjusted according to the test results of the cell density optimization, and then seeded into 96-well plates with 100 μl of the cell suspension to each well. The cells were incubated in a 37° C., 100% relative humidity, 5% $CO_2$ incubator for 24 hours.

b) The test compound was diluted with the medium to the corresponding action concentrations set up, and added into the cells in the plates at 25 μl/well. The test compound was prepared in 9 final action concentrations, which were obtained by sequentially diluted from 500 nM using twice echelon dilution.

c) The cells were incubated in a 37° C., 100% relative humidity, 5% $CO_2$ incubator for 72 hours.

d) The medium was removed from the cells, and a complete medium containing 10% CCK-8 was added and incubated in a 37° C. incubator for 1-4 hours.

e) After gentle shaking, the absorbance at 450 nm of the sample was measured on a SpectraMax M5 Microplate Reader, and the inhibition ratio was calculated using the absorbance at 650 nm as reference.

Data Processing

The inhibition ratio of the drug on tumor cell growth was calculated as follows: tumor cell growth inhibition %=[(Ac−As)/(Ac−Ab)]×100%

As: OA of sample (cell+CCK-8+test compound)

Ac: OA of negative control (cell+CCK-8+DMSO)

Ab: OA of positive control (medium+CCK-8+DMSO)

The IC50 curve was fitted and the IC50 value was calculated using the software Graphpad Prism 5 and using the calculation formula log(inhibitor) vs. normalized response-variable slope or log(inhibitor) vs. response-variable slope.

Experimental Results

This experiment tested the cytotoxic effects of 7 candidate compounds on 5 cell lines (MDA-MB-231, HT-1080, AGS, A-673 & HUVEC). The experimental results are shown in the following table.

TABLE 4

Determination of cytotoxicity IC50 values of 7 compounds against 5 cell lines

| Cell strain | Compound 7 | Compound 10 | Compound 12 | Compound 13 | Compound 15 | Compound 17 | Compound 18 | (−) phenylahistin |
|---|---|---|---|---|---|---|---|---|
| HT-1080 | 43.57 nM | 223.6 nM | 136.5 nM | ND | 78.85 nM | 14.57 nM | ND | >600 nM |
| AGS | 42.97 nM | 94.93 nM | 35.29 nM | ND | 63.52 nM | 10.83 nM | ND | >600 nM |
| A673 | 35.37 nM | 164.6 nM | 37.29 nM | ND | 94.90 nM | 7.255 nM | ND | >600 nM |
| HUVEC | 94.86 nM | 362.7 nM | 43.09 nM | ND | 78.61 nM | 34.96 nM | ND | >600 nM |
| MDA-MB-231 | 39.53 nM | 104.7 nM | 45.54 nM | ND | 122.9 nM | 20.38 nM | ND | >600 nM |

The results indicate that the above compounds have strong inhibitory effects on the examined tumor cell lines. Compared with the reference drug (−)phenylahistin (commercially available), the tested compounds in present invention have much better inhibitory activity on tumors. (see Table 4).

Example 15: Inhibitory Effect on Tumor Proliferation

Experimental Method

MES-SA cells (derived from ATCC) were cultured in low concentration of adriamycin for a long time to maintain sufficient cell viability and induced the expression of p-glycoprotein. After culturing for 10 months, the results of induced expression were detected by WB. After successful induction, the cells were cultured for one week in adriamycin-free medium. The tumor cells with adjusted concentration were inoculated into the armpit of nude mice. The transplanted tumors were treated with different drugs when they grew to a certain volume. Different doses of different drugs were administered to blank mice to explore the drug dose not affecting the body weight of the animals, namely the dose to be administered to treat the animals with transplanted tumors.

Figure 1:
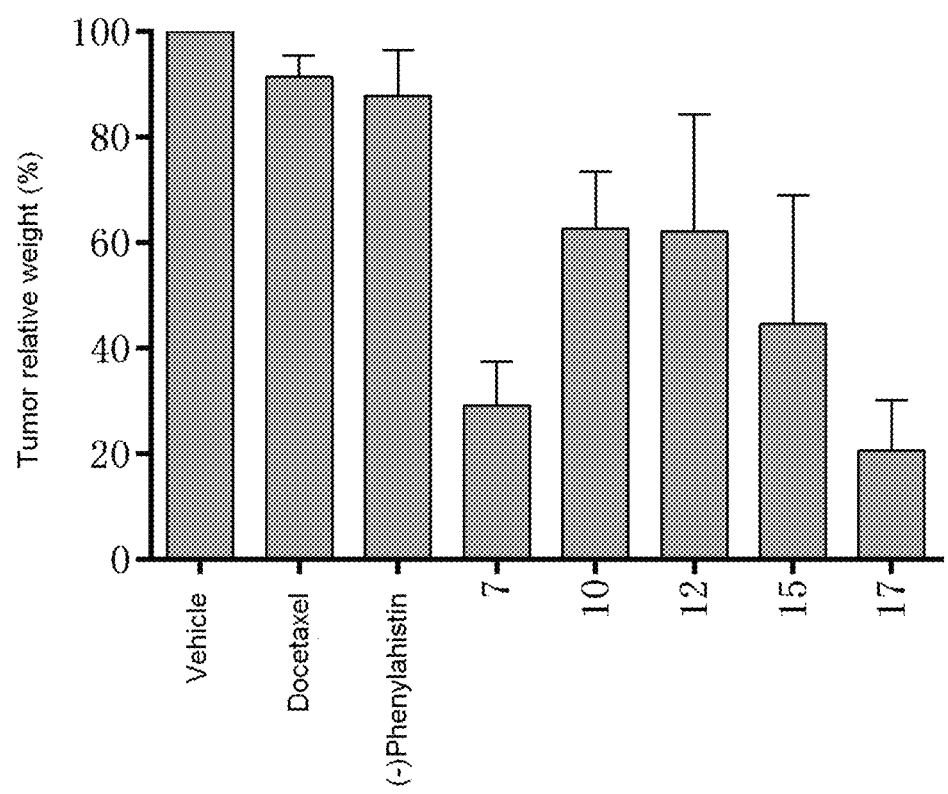
FIG. 1 shows the effect of each compound on tumor weight of drug-resistant MES-SA nude mice under an equivalent safe dose.

The results show that when administered at a dose that does not reduce the body weight of the animals, different drugs have certain differences in tumor inhibition rate in nude mice. Among them, (−)phenylahistin almost had no effect against tumor proliferation when used alone at a non-toxic dose. And docetaxel (commercially purchased) had a relatively poor pharmacodynamic effect at a dose without significant toxicity. Compared with the blank vehicle group, compound 7, compound 10, compound 12, compound 15 and compound 17 can effectively exert anti-tumor proliferation effects at a dose that has no significant effect on the body weight gain of the animals ($P<0.01$, Dunnet-t) (FIG. 1).

In this example, the effects of drugs on blood flow distribution of different tissues and organs at the same pharmacodynamic dose were simultaneously tested. Two hours after administration, the distribution of blood flow, including the one in the tumor tissue, of the docetaxel group was similar to that of the blank vehicle group. However, compound 7, compound 10, compound 12, compound 15, compound 17 and (−)phenylahistin did not significantly affect the distribution of blood flow in tissues except tumor tissues. Compound 7, compound 10, compound 12, compound 15, compound 17 and (−)phenylahistin groups can significantly reduce the intratumoral blood flow distribution in the tumor tissues, compared with the blank vehicle group.

Example 16: Antitumor Effect and Safety of the Compounds

The nude mice inoculated with tumor cells were administrated with blank vehicle, docetaxel, compound 17 as well as the combination drug of docetaxel and compound 17. The tumor volume was measured at different time period after the administration and the change of tumor volume was evaluated. At the same time, the change of body weight of the nude mice was examined to evaluate the antitumor effect and the toxicity degree of the drug. In addition, based on the above administration and grouping methods, the blood neutrophil count level for normal SD rats was measured before administration and after the final administration to evaluate the influence of the drug on neutrophil counts.

Figure 2:
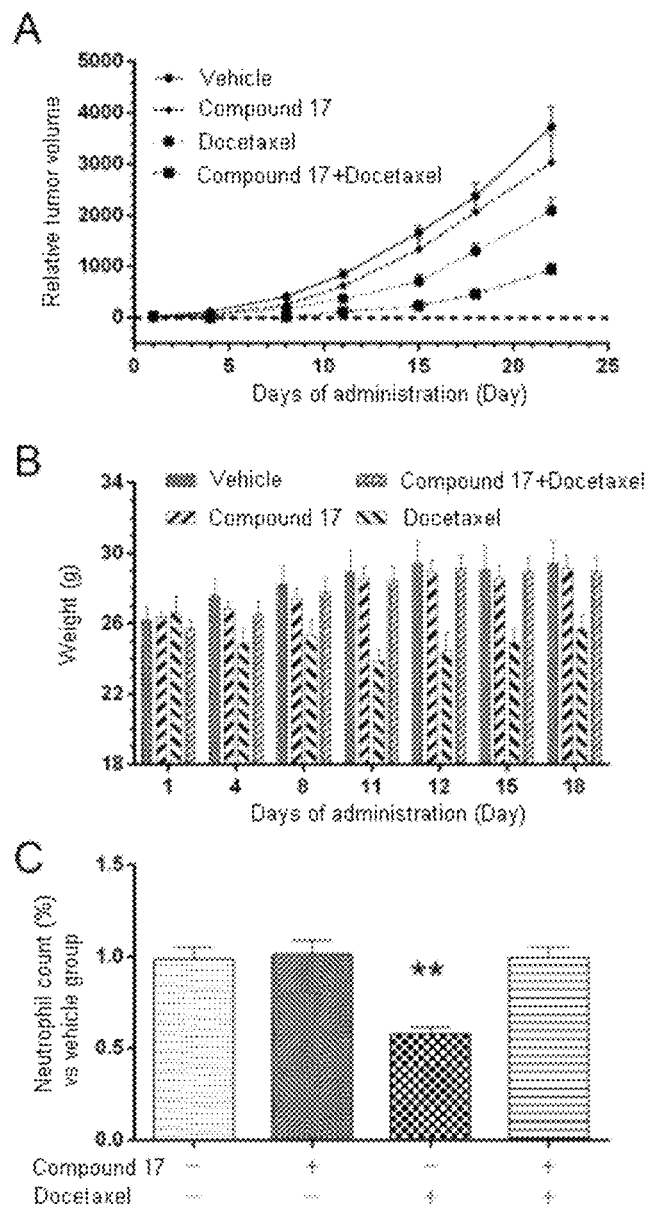
FIG. 2 shows the antitumor effect and safety test results of compound (17), in the figure.

The experimental results show that compound 17 can effectively inhibit the proliferation of tumor in vivo. Its anti-tumor activity is significantly enhanced when combined with docetaxel. The combination regimen effectively reduces the overall adverse effects of docetaxel as a single drug treatment, specifically reducing the weight loss of animals caused by the toxicity of docetaxel. After administrating the combination of docetaxel and compound 17 to normal rats, the neutrophil count was significantly increased in comparison with the using docetaxel alone. The adverse effect related to neutrophil count decrease caused by docetaxel is effectively relieved. By a comprehensive comparison, the effect of compound 17 against tumors was remarkable superior to that of docetaxel at doses having no influence on the overall physical state of the animals. That is, the tumor treatment window of compound 17 is remarkably surpasses docetaxel. Meanwhile, the combination of docetaxel and compound 17 can effectively reduce the toxicity of docetaxel and enhance the anti-tumor effect (FIG. 2).

Example 17: Effect on the Neutrophil Count

Experiment Method

Multiple doses of different drugs were administered to the nude mice respectively and the potency of the drugs in inhibiting the transplanted tumor in the nude mice was investigated. Base on the investigation, the equivalent dose of each drug was identified and converted to rat dose before administrated to the rats. That is, by administrating the rats with relatively equivalent pharmacodynamic dose, the effect of the drugs on the neutrophil count was examined. After continuously administration for two weeks, blood samples were collected and neutrophil counts were measured (FIG. 3).

The results show that after continuous administration of each compound to the rats at an equivalent pharmacodynamic dose, the conventional antitumor drug docetaxel can significantly reduce the neutrophil count in the rats, and the rats was observed to be not in physical state. Compared with docetaxel, (−)phenylahistin had a lower effect of reducing neutrophils at an equivalent pharmacodynamic dose, but the neutrophil count was still significantly lower than blank vehicle group and treatment groups ($P<0.01$, Dunnet-t). However, Compound 7, Compound 10, Compound 12, Compound 15 and Compound 17 groups had no obvious effect on neutrophils at an equivalent pharmacodynamic dose to other drugs ($P>0.05$, Dunnet-t). Therefore, Compound 7, Compound 10, Compound 12, Compound 15, and Compound 17 can effectively prevent the adverse reaction of neutrophil decrease while inhibiting the tumor proliferation. The variation trend of the animal body weight is positively correlated with the percentage of the neutrophil count change.

Example 18: Action on Microtubule Function

Human umbilical vein endothelial cells (HuVEC from Cambrex) were used in this study. The α-tubulin was stained and the effects of compounds 7, 10, 12, 15, 17 and tert-butyl-phenylahistin on tubulin were evaluated, in comparison with colchicine and paclitaxel.

Microtubule depolymerization (expressed by the lack of intact microtubule structure) and cell membrane blebbing (a clear indication of apoptosis) were induced in the HuVEC cells when exposed to compounds 7, 10, 12, 15, 17, tert-butyl-phenylahistin or colchicine (all at 2 µM) for 30 minutes in contrast to that observed in the DMSO control. Paclitaxel did not induce microtubule depolymerization under these conditions. Colchicine is a known microtubule depolymerization agent whereas paclitaxel is a tubulin stabilizing agent. Similar results can be observed when CCD-27sk cells were exposed to compounds 7, 10, 12, 15, 17 or colchicine.

Example 19: Pharmaceutical Composition

The compounds of the present invention may be combined with a physiologically acceptable carrier or vehicle to provide a pharmaceutical composition, such as lyophilized powder in the dosage form of tablet or capsule with various fillers and binders. Similarly, the compounds can be co-administered with other drugs. Co-administration denotes the administration of at least two drugs to a patient so as to obtain the combined effect of the drugs. For example, the drugs can be administered simultaneously or sequentially over a period of time. The effective dosage of a compound in the composition can be determined by the skilled in the art from their experiences in a wide range. Moreover, the compounds of the present invention can be used alone or in combination with one or more additional drugs depending on the indications and the desired therapeutic effect. The contemplated combination therapies in the present invention include the administration of the inventive compound together with additional drugs in a single pharmaceutical formulation as well as in separate pharmaceutical formulations.

The compounds of the present invention can be administered alone, or with a pharmaceutically acceptable carrier or dilute agent, optionally together with known adjuvants such as microcrystalline cellulose in a pharmaceutical composition. The compounds or above mentioned composition can be administered to mammals, preferably human beings according to the standard pharmaceutical practice. The route of the administration is oral or parenteral administration, including intravenous, intramuscular, intraperitoneal, subcutaneous, rectal and topical administration route.

For the oral administration of the chemotherapeutic compounds of the present invention, the selected compounds may be administered, for example, in the form of tablets, capsules, aqueous solution or suspension. Commonly used carriers including lactose and corn starch, and the lubricating agents such as magnesium stearate are usually added into the oral tablets. For the oral application of the capsules, the diluents including lactose and dry corn starch may be used. When aqueous suspension is required for oral application, the active ingredient is mixed with emulsifying agents and suspending agents. If desired, certain sweetening agents and/or flavoring agents may be added. For intramuscular, intraperitoneal, subcutaneous or intravenous application, the total concentration of the solutes should be controlled in order to obtain isotonic formulations.

19.1 Pharmaceutical Composition Containing Compound 17

Formulation 1

| | |
|---|---|
| Compound 17 | 2 mg |
| Docetaxel | 4 mg |
| Microcrystalline cellulose | 80 mg |
| Lactose | 98 mg |
| Low substituted hydroxypropyl cellulose | 1 mg |
| Magnesium stearate | 2 mg |
| Total | 187 mg |

Formulation 2:

| | |
|---|---|
| Compound 17 | 4 mg |
| Docetaxel | 8 mg |
| Microcrystalline cellulose | 80 mg |
| Lactose | 98 mg |
| Cross-linked sodium carboxymethylcellulose | 8 mg |
| Magnesium stearate | 2 mg |
| Total | 200 mg |

Formulation 3:

| | |
|---|---|
| Compound 17 | 10 mg |
| Docetaxel | 20 mg |
| Microcrystalline cellulose | 80 mg |
| Lactose | 100 mg |
| Cross-linked polyvidone | 8 mg |
| Magnesium stearate | 2 mg |
| Total | 215 mg |

Formulation 4:

| | |
|---|---|
| Compound 17 | 20 mg |
| Docetaxel | 40 mg |
| Lactose | 150 mg |
| Cross-linked polyvidone | 8 mg |
| Magnesium stearate | 2 mg |
| Total | 220 mg |

Formulation 5:

| | |
|---|---|
| Compound 17 | 20 mg |
| Docetaxel | 40 mg |
| Microcrystalline cellulose | 80 mg |
| Lactose | 98 mg |
| Magnesium stearate | 2 mg |
| Total | 240 mg |

Formulation 6:

| | |
|---|---|
| Compound 17 | 40 mg |
| Docetaxel | 80 mg |
| Microcrystalline cellulose | 80 mg |
| Lactose | 98 mg |
| Cross-linked polyvidone | 5 mg |
| Magnesium stearate | 2 mg |
| Total | 305 mg |

Formulation 7:

| | |
|---|---|
| Compound 7 | 80 mg |
| Docetaxel | 160 mg |
| Microcrystalline cellulose | 80 mg |
| Lactose | 98 mg |
| Cross-linked polyvidone | 5 mg |
| Magnesium stearate | 2 mg |
| Total | 425 mg |

19.2 Preparation Method of the Compositions

The active compound of the present invention, the disintegrating agents and the fillers were taken in proportion, passed through 60-100 mesh sieve, and mixed homogeneously. 2-20% polyvidone K30 solution in ethanol was used to prepare the wetting mass, which is pelletized and passed through 20-50 mesh sieve, then dried at 40-90° C. until the particle moisture to be controlled within 3%. After the breaking process, the granules were mixed with certain amount of lubricant to homogeneous and tableting.

Particularly, the pharmaceutical compositions of the above example may also be prepared by the following method: Compound 17, 7, the fillers and the disintegrants, which are 50 times of the prescribed amount, passed through 60 and 80 mesh sieves sequentially, and mixed uniformly. 2-20% polyvidone K30 solution in 50% ethanol was used to prepare the wetting mass, which is pelletized through 30 mesh sieve and dried at 60° C. until the particle moisture to be controlled within 3%. After a breaking process with 20 mesh sieve, the granules were mixed with certain amount of lubricant to homogeneous and tableting.

Example 20: Stability Investigation

The obtained compound 17 was subjected to stability investigation (10-day accelerated test). The tested conditions included 40° C., 60° C., humidity 75%, humidity 92.5%, and light. And under each condition, moisture, purity, maximum single impurity and total impurity of the compound tested were compared to that of day 0. The results show that the obtained compound is stable. However, (−)phenylahistin was degraded obviously at 60° C., indicating that high temperature has an influence on the stability of (−)phenylahistin.

TABLE 5

Results of stress testing of compound 17

Stress testing sample
No. of compound 17: 1 (prepared in Example 1)

| | | Moisture (%) | Content (%) | Maximum single impurity (%) | Total impurity (%) |
|---|---|---|---|---|---|
| Day 0 | 1 | 0.1 | 99.8 | 0.03 (RRT: 0.31) | 0.06 |
| Day 5 | 1-40° C. | 0.1 | 100.9 | 0.02 (RRT: 0.31) | 0.05 |
| | 1-60° C. | 0.2 | 99.0 | 0.03 (RRT: 0.31) | 0.06 |
| | 1-75% | 0.2 | 99.5 | 0.02 (RRT: 0.32) | 0.07 |
| | 1-92.5% | 0.3 | 99.5 | 0.02 (RRT: 0.31) | 0.07 |
| | 1-light | 0.1 | 100.3 | 0.04 (RRT: 0.31) | 0.07 |
| Day 10 | 1 | 0.1 | 100.4 | 0.03 (RRT: 0.31) | 0.08 |
| | 1-40° C. | 0.1 | 100.5 | 0.04 (RRT: 0.31) | 0.07 |
| | 1-60° C. | 0.2 | 99.7 | 0.03 (RRT: 0.31) | 0.08 |
| | 1-75% | 0.2 | 99.0 | 0.04 (RRT: 0.31) | 0.11 |
| | 1-92.5% | 0.3 | 99.4 | 0.03 (RRT: 0.31) | 0.08 |
| | 1-light | 0.1 | 99.6 | 0.04 (RRT: 0.31) | 0.09 |

TABLE 6

Results of stress testing of (−)phenylahistin

| Sample | Investigation condition | Content (%) | Maximum single impurity (%) |
|---|---|---|---|
| (−)Phenylahistin (Outsourcing) | Day 0 | 99.37 | 0.39 (RRT: 0.58) |
| | 60° C., day 5 | 95.77 | 2.84 (RRT: 0.24) |
| | 40° C., day 5 | 97.86 | 0.73 RRT: 0.58) |
| | 60° C., day 10 | 93.45 | 3.97 (RRT: 0.24) |
| | 40° C., day 10 | 98.36 | 1.22 (RRT: 0.58) |

The above description is not intended to limit the scope of the invention, any variants based on modifications and changes, which do not substantially differs from the general principles of current invention, should still fall into the scope of the current invention and should not be considered as new.

What is claimed is:

1. A compound represented by Formula (I):

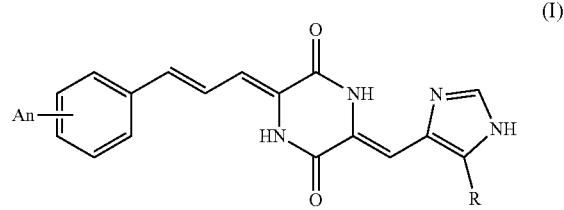

wherein:

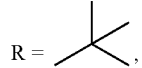

n independently represents an integer of 0 to 5, with the proviso that n≤5, A represents a mono- or poly-substituted group selected from the group consisting of H, $C_1$-$C_{20}$ alkyl, $C_1$-$C_{20}$ hydrocarbyl, $C_1$-$C_{20}$ acylamino, $C_1$-$C_{20}$ acyloxy, $C_1$-$C_{20}$ alkanoyl, $C_1$-$C_{20}$ alkoxycarbonyl, $C_1$-$C_{20}$ alkoxy, $C_1$-$C_{20}$ alkylamino, $C_1$-$C_{20}$ alkylcarboxyamino, aroyl, aralkanoyl, carboxyl, cyano, halogen, hydroxy, nitro and methylthienyl.

2. The compound according to claim 1, wherein n in the Formula (I) independently represents an integer of 0 to 2, with the proviso that n≤2, A represents a mono- or poly-substituted group selected from the group consisting of H, vinyl, methyl, trifluoromethoxy, methoxy, cyano, halogen and benzoyl.

3. The compound according to claim 1, selected from the group consisting of the following compounds:

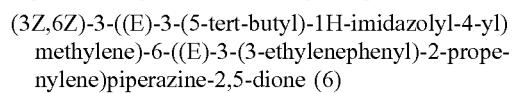
methylene)-6-((E)-3-(3-ethylenephenyl)-2-propenylene)piperazine-2,5-dione (6)

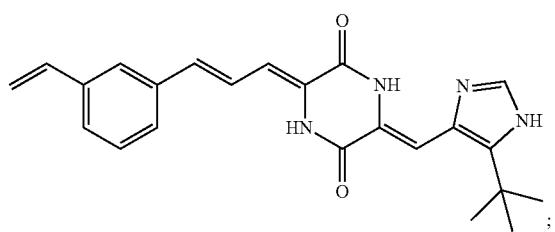 [SMILES: C=Cc1cccc(/C=C/C=c2\[nH]c(=O)/c(=C/c3nc[nH]c3C(C)(C)C)[nH]c2=O)c1]

(3Z,6Z)-3-((E)-3-(5-tert-butyl)-1H-imidazolyl-4-yl) methylene)-6-((E)-3-(3-fluorophenyl)-2-propenylene) piperazine-2,5-dione (7)

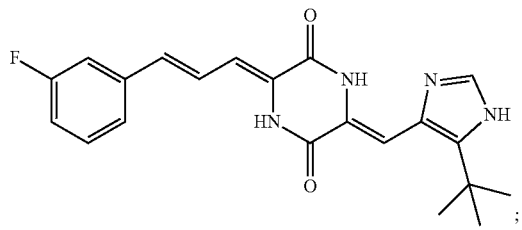 [SMILES: CC(C)(C)c1[nH]cnc1/C=c1\[nH]c(=O)/c(=C/C=C/c2cccc(F)c2)[nH]c1=O]

(3Z,6Z)-3-((E)-3-(5-tert-butyl)-1H-imidazolyl-4-yl) methylene)-6-((E)-3-phenyl propenylene)piperazine-2,5-dione (8)

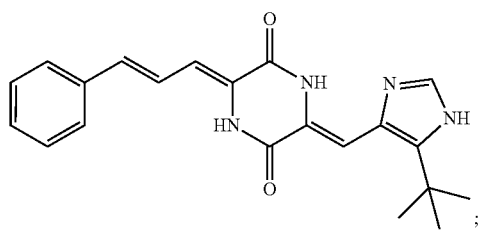 [SMILES: CC(C)(C)c1[nH]cnc1/C=c1\[nH]c(=O)/c(=C/C=C/c2ccccc2)[nH]c1=O]

(3Z,6Z)-3-((E)-3-(5-tert-butyl)-1H-imidazolyl-4-yl) methylene)-6-((E)-3-(2,3-dimethylphenyl)-2-propenylene)piperazine-2,5-dione (9)

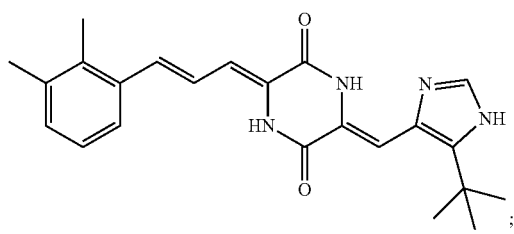 [SMILES: Cc1cccc(/C=C/C=c2\[nH]c(=O)/c(=C/c3nc[nH]c3C(C)(C)C)[nH]c2=O)c1C]

(3Z,6Z)-3-((E)-3-(5-tert-butyl)-1H-imidazolyl-4-yl) methylene)-6-((E)-3-(4-trifluoromethoxyphenyl)-2-propenylene)piperazine-2,5-dione (10)

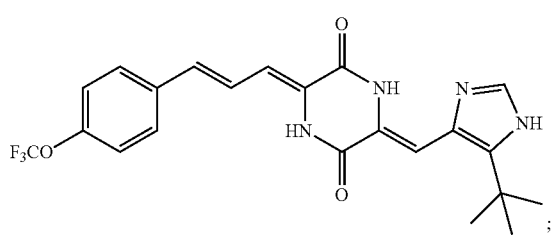 [SMILES: CC(C)(C)c1[nH]cnc1/C=c1\[nH]c(=O)/c(=C/C=C/c2ccc(OC(F)(F)F)cc2)[nH]c1=O]

(3Z,6Z)-3-((E)-3-(5-tert-butyl)-1H-imidazolyl-4-yl) methylene)-6-((E)-3-(2,5-difluorophenyl)-2-propenylene)piperazine-2,5-dione (11)

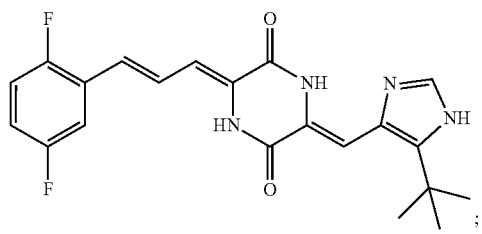 [SMILES: CC(C)(C)c1[nH]cnc1/C=c1\[nH]c(=O)/c(=C/C=C/c2cc(F)ccc2F)[nH]c1=O]

(3Z,6Z)-3-((E)-3-(5-tert-butyl)-1H-imidazolyl-4-yl) methylene)-6-((E)-3-(4-methoxyphenyl)-2-propenylene)piperazine-2,5-dione (12)

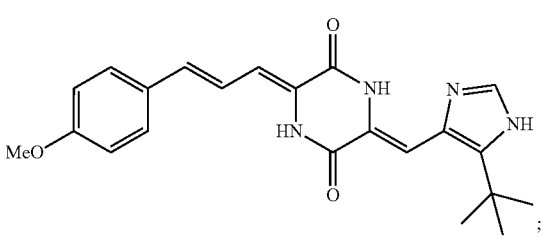 [SMILES: COc1ccc(/C=C/C=c2\[nH]c(=O)/c(=C/c3nc[nH]c3C(C)(C)C)[nH]c2=O)cc1]

(3Z,6Z)-3-((E)-3-(5-tert-butyl)-1H-imidazolyl-4-yl) methylene)-6-((E)-3-(3,5-dimethoxyphenyl)-2-propenylene)piperazine-2,5-dione (13)

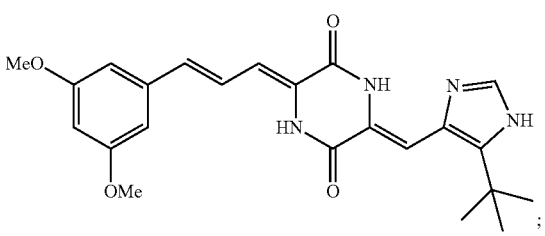 [SMILES: COc1cc(/C=C/C=c2\[nH]c(=O)/c(=C/c3nc[nH]c3C(C)(C)C)[nH]c2=O)cc(OC)c1]

(3Z,6Z)-3-((E)-3-(5-tert-butyl)-1H-imidazolyl-4-yl) methylene)-6-((E)-3-(3-chlorophenyl)-2-propenylene) piperazine-2,5-dione (14)

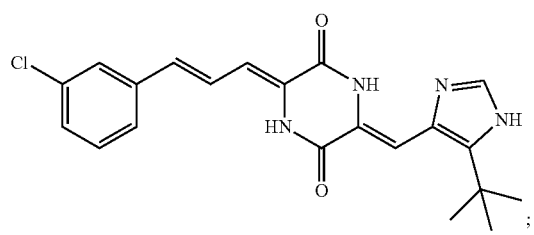 [SMILES: CC(C)(C)c1[nH]cnc1/C=c1\[nH]c(=O)/c(=C/C=C/c2cccc(Cl)c2)[nH]c1=O]

(3Z,6Z)-3-((E)-3-(5-tert-butyl)-1H-imidazolyl-4-yl) methylene)-6-((E)-3-(3-cyanophenyl)-2-propenylene) piperazine-2,5-dione (15)

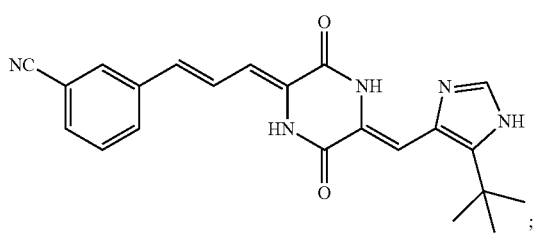 [SMILES: CC(C)(C)c1[nH]cnc1/C=c1\[nH]c(=O)/c(=C/C=C/c2cccc(C#N)c2)[nH]c1=O]

(3Z,6Z)-3-((E)-3-(5-tert-butyl)-1H-imidazolyl-4-yl)
methylene)-6-((E)-3-(3-benzoylphenyl)-2-prope-
nylene)piperazine-2,5-dione (16)

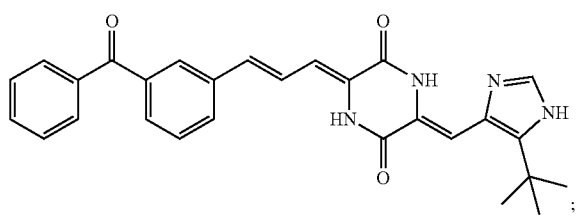 [SMILES: CC(C)(C)c1[nH]cnc1/C=c1\[nH]c(=O)/c(=C/C=C/c2cccc(C(=O)c3ccccc3)c2)[nH]c1=O]

(3Z,6Z)-3-((E)-3-(5-tert-butyl)-1H-imidazolyl-4-yl)
methylene)-6-((E)-3-(2-chloro-5-fluorophenyl)-2-pro-
penylene)piperazine-2,5-dione (17)

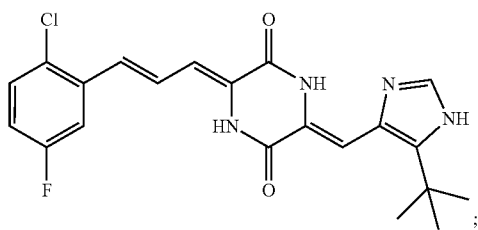

(3Z,6Z)-3-((E)-3-(5-tert-butyl)-1H-imidazolyl-4-yl)
methylene)-6-((E)-3-(3-methoxy-4-acetoxy)-2-prope-
nylene)piperazine-2,5-dione (18)

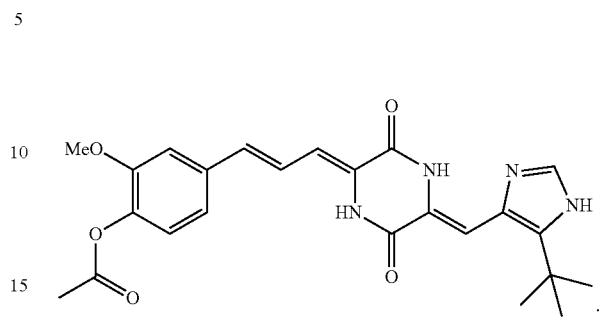

4. A pharmaceutical composition, comprising the compound of claim 1 and a pharmaceutically acceptable carrier and/or excipients.

5. A method for treatment of tumors comprising the step of administering to an individual the compound of claim 1.

6. The method of claim 5, wherein said compound is administered to the individual in combination with a chemotherapeutic agent.

7. The method according to claim 6, wherein the compound is (3Z, 6Z)-3-((E)-3-(5-tert-butyl)-1H-imidazolyl-4-yl)methylene-6-((E)-3-(2-chloro-5-fluorophenyl)-2-propenylene)piperazine-2,5-dione (17), and the chemotherapeutic agent is docetaxel.

* * * * *